United States Patent
Sherman et al.

(10) Patent No.: US 8,428,672 B2
(45) Date of Patent: Apr. 23, 2013

(54) MEDICAL VENTILATOR WITH AUTONOMOUS CONTROL OF OXYGENATION

(75) Inventors: Leslie H. Sherman, Denville, NJ (US); George Beck, Mendham, NJ (US); Dorian LeCroy, New York, NY (US)

(73) Assignee: Impact Instrumentation, Inc., West Caldwell, NJ (US)

( * ) Notice: Subject to any disclaimer, the term of this patent is extended or adjusted under 35 U.S.C. 154(b) by 476 days.

(21) Appl. No.: 12/696,176

(22) Filed: Jan. 29, 2010

(65) Prior Publication Data

US 2010/0186742 A1    Jul. 29, 2010

Related U.S. Application Data

(60) Provisional application No. 61/148,069, filed on Jan. 29, 2009.

(51) Int. Cl.
*A61B 5/00* (2006.01)
(52) U.S. Cl.
USPC .......................................... 600/322; 600/323
(58) Field of Classification Search .................. 600/323, 600/322, 326, 328, 301; 128/204.22, 204.23, 128/204.21, 205.11, 204.25
See application file for complete search history.

(56) References Cited

U.S. PATENT DOCUMENTS

| | | | |
|---|---|---|---|
| 4,326,513 A | 4/1982 | Schulz et al. | |
| 4,651,731 A | 3/1987 | Vicenzi et al. | |
| 4,889,116 A | 12/1989 | Taube | |
| 4,986,268 A | 1/1991 | Tehrani | |
| 5,103,814 A | 4/1992 | Maher | |
| 5,251,632 A | 10/1993 | Delpy | |
| 5,365,922 A | 11/1994 | Raemer | |
| 5,388,575 A | 2/1995 | Taube | |
| 6,186,142 B1 | 2/2001 | Schmidt et al. | |
| 6,192,883 B1 | 2/2001 | Miller, Jr. | |
| 6,512,938 B2 | 1/2003 | Claure et al. | |
| 6,591,835 B1 | 7/2003 | Blanch | |
| 6,671,529 B2 | 12/2003 | Claure et al. | |
| 6,761,165 B2 | 7/2004 | Strickland, Jr. | |
| 6,786,217 B2 | 9/2004 | Stenzler | |
| 6,789,539 B2 | 9/2004 | Martinez | |
| 6,796,305 B1 | 9/2004 | Banner et al. | |
| 6,796,306 B2 | 9/2004 | Martinez | |
| 6,810,876 B2 | 11/2004 | Berthon-Jones | |
| 6,814,076 B2 | 11/2004 | Shusterman et al. | |
| 6,823,866 B2 | 11/2004 | Jafari et al. | |
| 6,840,240 B1 | 1/2005 | Berthon-Jones et al. | |
| 6,845,773 B2 | 1/2005 | Berthon-Jones et al. | |
| 6,848,444 B2 | 2/2005 | Smith et al. | |
| 6,849,049 B2 | 2/2005 | Starr et al. | |

(Continued)

OTHER PUBLICATIONS

Johannigman JA, Muskat P. Barnes S et al. Autonomous control of oxygenation. J Trauma 2008; 64 (4 Suppl): S295-301.

*Primary Examiner* — Nicholas Lucchesi
*Assistant Examiner* — Pritesh Patel
(74) *Attorney, Agent, or Firm* — Gerald E. Hespos; Michael J. Porco; Matthew T. Hespos (57) ABSTRACT

A portable critical care medical ventilator with autonomous control of oxygenation is provided. The system and method provide for significantly reducing the $O_2$ required to maintain an adequate $O_2$ concentration and as a result delivery of $O_2$ to the body's tissues and does not require the clinician to enter initial values.

25 Claims, 4 Drawing Sheets

U.S. PATENT DOCUMENTS

| | | |
|---|---|---|
| 6,851,426 B1 | 2/2005 | Stromberg |
| 6,854,462 B2 | 2/2005 | Berthon-Jones et al. |
| 6,866,040 B1 | 3/2005 | Bourdon |
| 6,868,346 B2 | 3/2005 | Larson et al. |
| 7,008,380 B1 * | 3/2006 | Rees et al. .................... 600/532 |
| 7,201,734 B2 | 4/2007 | Hickle |
| 7,247,154 B2 | 7/2007 | Hickle |
| 7,527,054 B2 | 5/2009 | Misholi |
| 2003/0075178 A1 | 4/2003 | Claure |
| 2005/0109340 A1 | 5/2005 | Tehrani |

* cited by examiner

MEDICAL VENTILATOR WITH AUTONOMOUS CONTROL OF OXYGENATION

This application claims priority on U.S. Provisional Application No. 61/148,069 filed on Jan. 29, 2009.

BACKGROUND

1. Field of the Invention

The present disclosure relates generally to medical ventilator systems, and more particularly, to a medical ventilator with autonomous control of oxygenation.

2. Description of the Related Art

Achieving adequate oxygenation is one of the primary goals of mechanical ventilation. This goal is accomplished through the adjustment of the fraction of inspired oxygen concentration ($FIO_2$), positive end-expiratory pressure (PEEP), and mean airway pressure. Titration of these variables is guided by continuous noninvasive monitoring of oxygen saturation by pulse oximetry ($SpO_2$) and intermittent arterial blood sampling for arterial oxygen tension ($PaO_2$) and measured oxygen saturation ($SaO_2$). Traditional application of this technology has sought to maintain the $SpO_2$ between 98 and 100% to assure adequate oxygenation and prevent desaturation events ($SpO_2$<88%) which has been shown to have a deleterious effect on patient outcome. Previous work has focused on preventing hypoxemia and hyperoxia which has tended to maintain the $SpO_2$ on the flat portion of the oxyhemoglobin dissociation curve. Maintaining the $SpO_2$ in this area allows for transient changes in $PaO_2$ caused by shunting while maintaining $SpO_2$ and therefore the $O_2$ concentration in the blood.

Goals for oxygenation vary with specific disease states and philosophy of the attending health care personnel. In adults, adequate oxygenation is typically considered an $SaO_2$>90% and $PaO_2$>60 mm Hg. In neonates, where both hypoxia and hyperoxia are associated with adverse outcomes, arterial oxygen is more tightly controlled. Similarly, in patients with head injuries, even a single hypoxemic event is associated with poor outcome. In these patients, hyperoxia may be indicated both to prevent hypoxemia and to assure adequate brain tissue oxygenation. Previous automated control methods have required the clinician to enter an $SpO_2$ target and range of acceptable values. These methods presuppose the attending clinician is capable of determining what is best for the patient and adjusting the device accordingly.

Oxygen toxicity is a common concern in intensive care, but the effects of elevated $FIO_2$ in critically ill patients is controversial. A common goal of PEEP titration is reduction of $FIO_2$ to nontoxic levels (e.g., <0.60); however, the exact level of $O_2$ that may be construed as safe is unknown. In adults, the potential effects of hyperoxia are always preferable to the immediate effects of hypoxemia.

Although maintenance of adequate $O_2$ delivery and prevention of hypoxemia are the primary goals for the battlefield casualty, military medical operations have unique concerns. In civilian US hospitals, under normal conditions, $O_2$ reserves are plentiful. In military medical and flight operations, $O_2$ is a limited resource that needs to be conserved. During deployed military medical operations, the logistical considerations required to provide and sustain $O_2$ resources in forward areas are considerable. It has been estimated that $O_2$ containers and $O_2$ generation equipment comprise approximately fifteen to thirty percent of the entire logistical footprint of weight and space (cube) necessary to provide medical care in the field during combat operations. These considerations become even more acutely focused during transport when both the patient, medical equipment and $O_2$ need to be moved in air and ground vehicles that are called into service to move the casualty. Mission length can vary depending upon the tactical and strategic consideration(s) of the theater and the criticality of the patient. The necessity of accounting for potential required $O_2$ resources as well as the physical transport of $O_2$ tanks and liquid $O_2$ is an important component of any mission. Mission planning commonly involves a calculation of required $O_2$ needs and then doubling that value as a margin of safety. Similar $O_2$ supply problems exist with mass casualty incidents and disaster relief. These applications have needs that are very similar to the military's. Immediately following hurricane Katrina for example, affected area hospitals ran out of $O_2$ as did the few ambulances that supported the evacuations from the area. Florida had similar situations following its hurricanes: (1) the loss of electrical power prevented hospitals from distributing gaseous $O_2$ from their liquid $O_2$ tanks, (2) downed electrical lines prevented restoration of power which prevented the use of $O_2$ concentrators and, (3) power lines and trees blocked roads which prevented deliveries of bottled gaseous $O_2$. Also, rural areas that routinely transport patients over great distances to hospitals sometimes take in excess of 4 hours which could marginalize supplies of on-board $O_2$.

Given the preceding considerations, it would seem apparent that $O_2$ conservation takes on greater importance in pre-hospital and transport environments. In these environments the goals of $O_2$ therapy are to prevent hypoxemia, to assure adequate arterial oxygenation and to minimize $O_2$ usage.

SUMMARY

A portable critical care medical ventilator with autonomous control of oxygenation is provided. The system and method provides for significantly reducing the $O_2$ required to maintain an adequate $O_2$ concentration and as a result delivery of $O_2$ to the body's tissues and does not require the clinician to enter initial values.

According to one aspect of the present disclosure, a method for delivering $O_2$ to a patient with a mechanical ventilator includes (a) supplying fractionally inspired oxygen ($FIO_2$) to a patient based on a target $O_2$ saturation ($SpO_2$), wherein the target $SpO_2$ is set a lower limit of clinical acceptability of $SpO_2$ for the patient to conserve $O_2$; (b) monitoring $SpO_2$ returned from the patient; (c) determining an error between the monitored $SpO_2$ and the target $SpO_2$ and while the error is greater than a predetermined error iteratively performing, (d) determining a gain factor such that increases to $FIO_2$ are greater than decreases for a magnitude of the determined error; (e) determining a correction factor by multiplying the determined gain factor by the magnitude of the error; and (f) applying the corrector factor to the supplied $FIO_2$. In one aspect, the method waits a first predetermined time period before iteratively performing steps (c)-(f).

In another aspect, the gain factor is determined such that increases to $FIO_2$ are three times as great as decreases for the magnitude of the determined error.

According to a further aspect of the present disclosure, a system for delivering $O_2$ to a patient is provided. The system includes a ventilator for supplying fractionally inspired oxygen ($FIO_2$) to a patient based on a target $O_2$ saturation ($SpO_2$), wherein the target $SpO_2$ is set to the lower limit of clinical acceptability of $SpO_2$ for the patient to conserve $O_2$; and an $O_2$ concentrator coupled to the ventilator for supplying $O_2$ to the ventilator, wherein the ventilator monitors $SpO_2$ returned from the patient, determines an error between the monitored $SpO_2$ and the target $SpO_2$ and while the error is greater than a predetermined error, the ventilator iteratively determines a gain factor such that increases to $FlO_2$ are greater than decreases for a magnitude of the determined error, determines a correction factor by multiplying the determined gain factor by the magnitude of the error and applies the corrector factor to the supplied $FlO_2$. The system further includes a patient ventilation circuit including a supply tube for supplying $FlO_2$ to the patient from the ventilator and a bidirectional connection for sending sensed or measured parameters of the patient to the ventilator.

In one aspect, the ventilator controls an output of the $O_2$ concentrator to maintain the corrected supplied $FlO_2$. In another aspect, the ventilator mixes the output of the $O_2$ concentrator with ambient air to maintain the corrected supplied $FlO_2$.

BRIEF DESCRIPTION OF THE DRAWING

The above and other aspects, features, and advantages of the present disclosure will become more apparent in light of the following detailed description when taken in conjunction with the accompanying drawings.

DETAILED DESCRIPTION

To facilitate understanding, identical reference numerals have been used, where possible to designate identical elements that are common to the figures, except that alphanumerical suffixes may be added, when appropriate, to differentiate such elements. The images in the drawings are simplified for illustrative purposes and are not depicted to scale.

The appended drawings illustrate exemplary embodiments of the present disclosure and, as such, should not be considered as limiting the scope of the disclosure that may admit to other equally effective embodiments. Correspondingly, it has been contemplated that features or steps of one embodiment may beneficially be incorporated in other embodiments without further recitation.

In some embodiments, particular method steps of the discussed methods are performed in the depicted order. In alternate embodiments, in the respective methods, at least two method steps or portions thereof may be performed contemporaneously, in parallel, or in a different order.

This description is presented as an example of the principles of the invention. It will be appreciated that those skilled in the art will be able to devise various other arrangements that embody the principles of the disclosure and that are included within the spirit and scope of this invention.

All examples and conditional language recited herein are intended for teaching purposes to aid the reader in understanding the principles of the disclosure and the concepts contributed by the inventor to furthering the art, and are to be construed as being without limitation to such specifically recited examples and conditions.

Moreover, all statements herein reciting principles, aspects and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, those skilled in the art who have read this application will appreciate that the block diagrams presented herein represent conceptual views of illustrative circuitry embodying the principles of the disclosure. Similarly, it will be appreciated that any flow charts, flow diagrams, state transition diagrams, pseudo-code, and the like represent various processes which may be substantially represented in computer readable media and so executed by a computer or processor, whether or not such computer or processor is explicitly shown.

The functions of the various elements shown in the figures may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor ("DSP") hardware, read only memory ("ROM") for storing software, random access memory ("RAM"), and nonvolatile storage, programmable logic or other device or devices.

Other hardware, conventional and/or custom, may also be included. Similarly, any switches shown in the figures are conceptual only. Their function may be carried out through the operation of program logic, through dedicated logic, through the interaction of program control and dedicated logic, or even manually, the particular technique being selectable by the implementer as more specifically understood from the context.

The word "exemplary" is used herein to mean "serving as an example, instance, or illustration." Any configuration or design described herein as "exemplary" is not necessarily to be construed as preferred or advantageous over other configurations or designs. Herein, the phrase "coupled with" is defined to mean directly connected to or indirectly connected with through one or more intermediate components. Such intermediate components may include both hardware and software based components.

Figure 1:
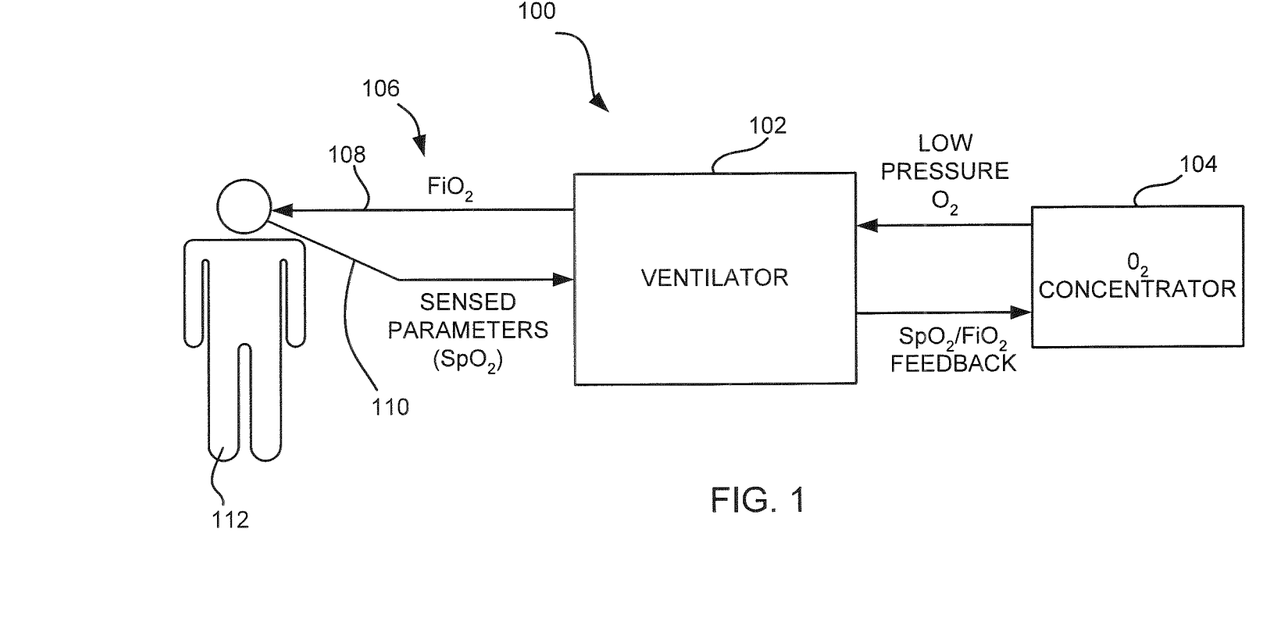
FIG. 1 is a diagram of a system for $O_2$ generation having closed loop control of $FlO_2$ in accordance with an embodiment of the present disclosure.

Referring to FIG. 1, a system 100 for $O_2$ generation having closed-loop control of $FlO_2$ is provided. The system 100 includes a ventilator 102 for providing ventilation and supplemental $O_2$ to a patient and an $O_2$ concentrator (typically providing 90%-96% $O_2$) 104 to the ventilator 102 for supplying to the ventilator 102 $O_2$. The system 100 further includes a patient ventilation circuit 106 which includes a supply tube 108 for supplying $FlO_2$ to the patient 112 and a bidirectional connection 110 for sending sensed or measured parameters of the patient to the ventilator 102. Although an $O_2$ concentrator 104 is shown in FIG. 1, the system 100 can use any source of medical oxygen, including liquid, chemical and gaseous sources.

Figure 2:
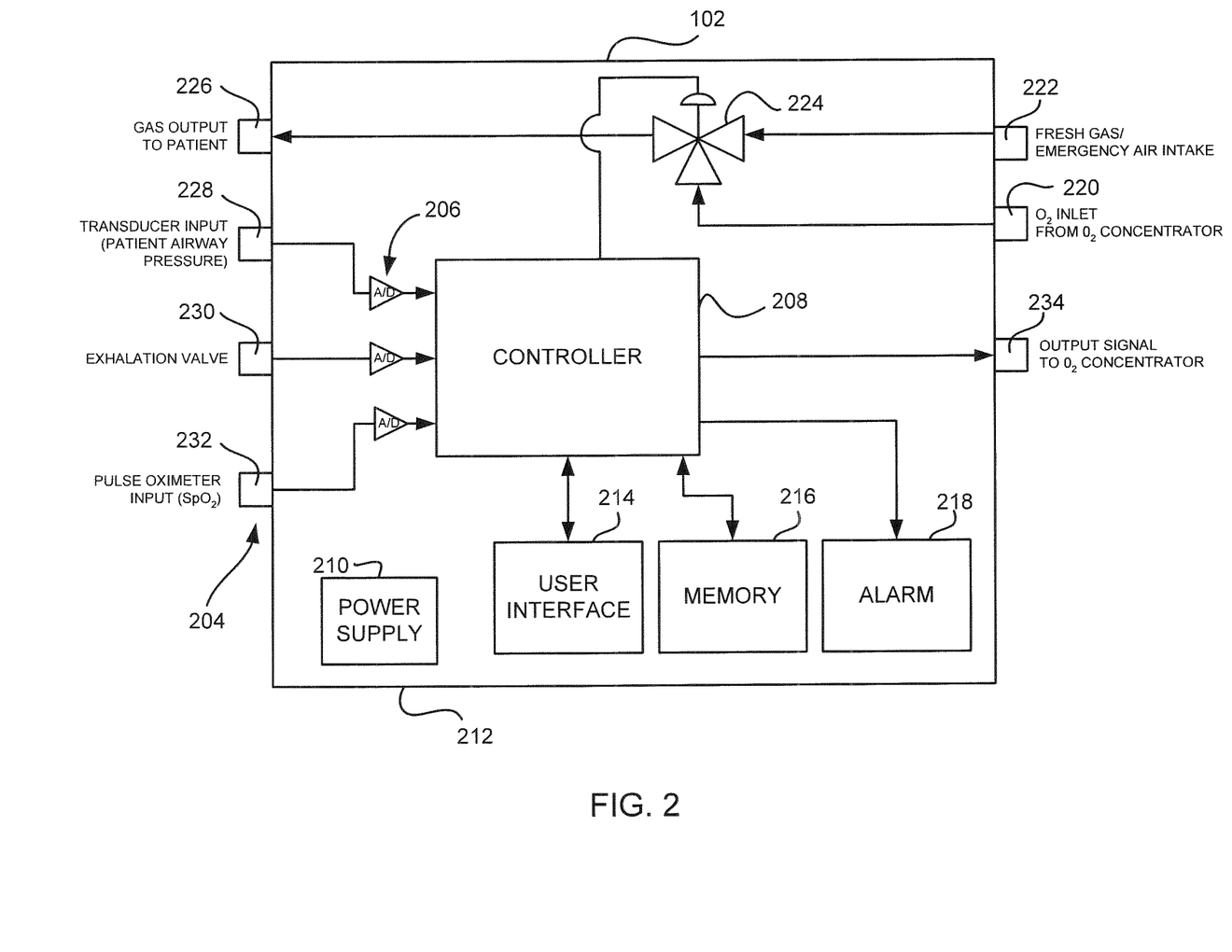
FIG. 2 is a block diagram of the ventilator in accordance with an embodiment of the present disclosure.

FIG. 2 illustrates a block diagram of the ventilator 102. Generally, the ventilator 102 includes input connections for a plurality of sensors 204, a plurality of analog-to-digital (ND) converters 206 for converting the inputted sensors into digital form and a controller 208 controlling an output of the ventilator 102 based on the sensed parameters of the inputs. In one embodiment, the controller 208 will include a central processing unit (CPU) and/or a digital signal processor (DSP). The controller 208 is configured for receiving the digital signals from the ND converters 206 to perform the necessary calculations for controlling the overall operations of the ventilator 102, including control of the $FIO_2$.

A power supply 210 is also provided for providing power to each component of the ventilator 102. In one embodiment, the power supply 210 is coupled to an external power source, e.g., 120V power source. In another embodiment, the power supply 210 is coupled to an internal rechargeable battery disposed in the housing 212 of the ventilator 102.

The ventilator 102 of the present disclosure will have user interface 216 for interacting with a user and for communicating events, alarms and instructions to the user. The user interface will include a display for providing visual indications to the user. The display may include a touch screen, a liquid crystal display (LCD), a plurality of LED number segments, individual light bulbs, a plasma screen display, a cathode ray tube display, an electroluminescent display an organic LED display or any combination of these. The display may provide the information to the user in the form of alpha-numeric lines, computer-generated graphics, videos, etc. Visual information provided on the display may include but is not limited to instructional videos, operating manuals associated with an Intelligent Electronic Device (IED), a flowchart for troubleshooting, a checklist for troubleshooting, etc. Digital files including the various visual instructions are stored in either memory 216 or retrieved from a remote event server.

The user interface 214 will also include an audible output device, e.g., a speaker. The speaker will be coupled to the controller 208 via a digital-to-analog converter (D/A) for converting digital audio files stored in memory 216 to analog signals playable by the speaker. The audible output device 24 may simply provide audible instructions to a user when an event is detected or may provide audio with a corresponding video being displayed on the display.

The ventilator 102 of the present disclosure will support various file types including but not limited to Microsoft Windows Media Video files (.wmv), Microsoft Photo Story files (.asf), Microsoft Windows Media Audio files (.wma), MP3 audio files (.mp3), JPEG image files (.jpg, .jpeg, .jpe, .jfif), MPEG movie files (.mpeg, .mpg, .mpe, .mp1v, .mp2v .mpeg2), Microsoft Recorded TV Show files (.dvr-ms), Microsoft Windows Video files (.avi) and Microsoft Windows Audio files (.wav).

The memory 216 is configured for storing files executable by the controller and for storing files for the visual and/or audible instructions. The memory 28 includes internal storage memory, e.g., random access memory (RAM), or removable memory such as magnetic storage memory; optical storage memory, e.g., the various known types of CD and DVD media; solid-state storage memory, e.g., a CompactFlash card, a Memory Stick, SmartMedia card, MultiMediaCard (MMC), SD (Secure Digital) memory; or any other memory storage that exists currently or will exist in the future. By utilizing removable memory, the ventilator 102 can be easily upgraded with new instruction files as needed.

In one embodiment, the digital audio files may be programmed directly through the ventilator 102. In this embodiment, the ventilator 102 will include an audio input device, e.g., a microphone, for receiving spoken words in the form of analog signals. The analog signals will then be sent to an analog-to-digital converter (A/D) to convert the analog signals into digital signals understandable by the controller 208. The controller 208 will then store the recorded digital audio file in the memory 216. The user may associate the recorded digital file with a particular alarm through the touch screen display. Alternatively, the user may associate the recorded digital file with an event code.

In a further embodiment, the ventilator 102 will include an alarm 218 separate from the user interface 214 for remotely indicating alarms to the user.

The ventilator 102 includes an inlet 220 for receiving $O_2$ from the $O_2$ concentrator 104 and a fresh gas/emergency air intake 222 which are both piped to an air/oxygen manifold 224. In one embodiment, the manifold combines the outputs of an $O_2$ valve and an air compressor. In another embodiment, the manifold may contain an $O_2$ and air valve or all three: air valve, $O_2$ valve and compressor. The controller 208 will modulate the output of the $O_2$ and air valves or an $O_2$ valve and compressor 224 to achieve a determined level of $FIO_2$ which will be supplied to a patient via the gas output 226. The controller 208 determines the required change in $FIO_2$ based on the input sensors 204, e.g., transducer input 228, exhalation valve input 230 and pulse oximeter input 232. An algorithm calculates the ratio of flow rates required from the $O_2$ valve and compressor to attain the required change in $FIO_2$ from the current $FIO_2$. An output port 234, e.g., a USB port, is provided to communicate to and control the $O_2$ concentrator 104 or other $O_2$ source.

The system 100 is designed to maintain oxygenation while at the same time minimizing $O_2$ use. This is accomplished by a predetermined control target that is at the lower limit of clinical acceptability that has been validated in clinical trials. Doing this assures that the patient is maintained at a safe limit using the least amount of $O_2$ which is of most importance in military and pre-hospital environments as described above. When used with an $O_2$ concentrator the approach also reduces the power required to maintain the patient by regulating the output of the concentrator. To safely manage patients at the lower limit of acceptable oxygenation, an asymmetric gain approach is employed. In this approach, the rate at which the delivered $O_2$ is decreased for a patient who has a saturation value greater than the target is less than the rate at which $O_2$ is increased when the saturation is less than the target value. Use of asymmetric gain is a practical compromise between maximal $O_2$ conservation and patient safety based on the differences in the time required to reach equilibrium for upward changes vs. downward changes that were observed in the preclinical and clinical trials. Additional time spent slightly above the $SpO_2$ target allows time for the lung and blood to reach equilibrium while only slightly increasing the amount of $O_2$ used to maintain adequate oxygenation. Decreasing the response time to $SpO_2$ values below the target minimizes the time spent outside of the therapeutic range. The approach is based on the slope of the oxyhemoglobin dissociation curve for $SpO_2$ of 94%. Small changes in arterial $O_2$ tension can have a dramatic affect on $SpO_2$. In addition, the algorithm has a wait state associated following each $FIO_2$ change where it monitors the convergence toward the target value. Time between changes is required to account for latencies for diffusion of $O_2$ from the lung to the blood and the transit time for blood from the lung to the peripheral capillary beds where the $SpO_2$ signal is measured. An additional control loop automatically increases the oxygenation target when the system determines that the patient's oxygenation is too unstable to be maintained at the current target value. Whenever there are two or more desaturation events ($SpO_2$<88%) in a 10 minute period, the system increases the $SpO_2$ target by 1%. In essence, this moves the patient to a flatter portion of the oxyhemoglobin dissociation curve where transient changes in arterial $O_2$ tension have a less dramatic affect on the blood oxygen concentration. Lastly, a safety control loop continuously monitors for desaturation events and automatically increase the $FlO_2$ to 100%. Working in parallel these approaches reduce the potential for oscillation which could result in transient hypoxemic and hyperoxemic events.

Figure 3:
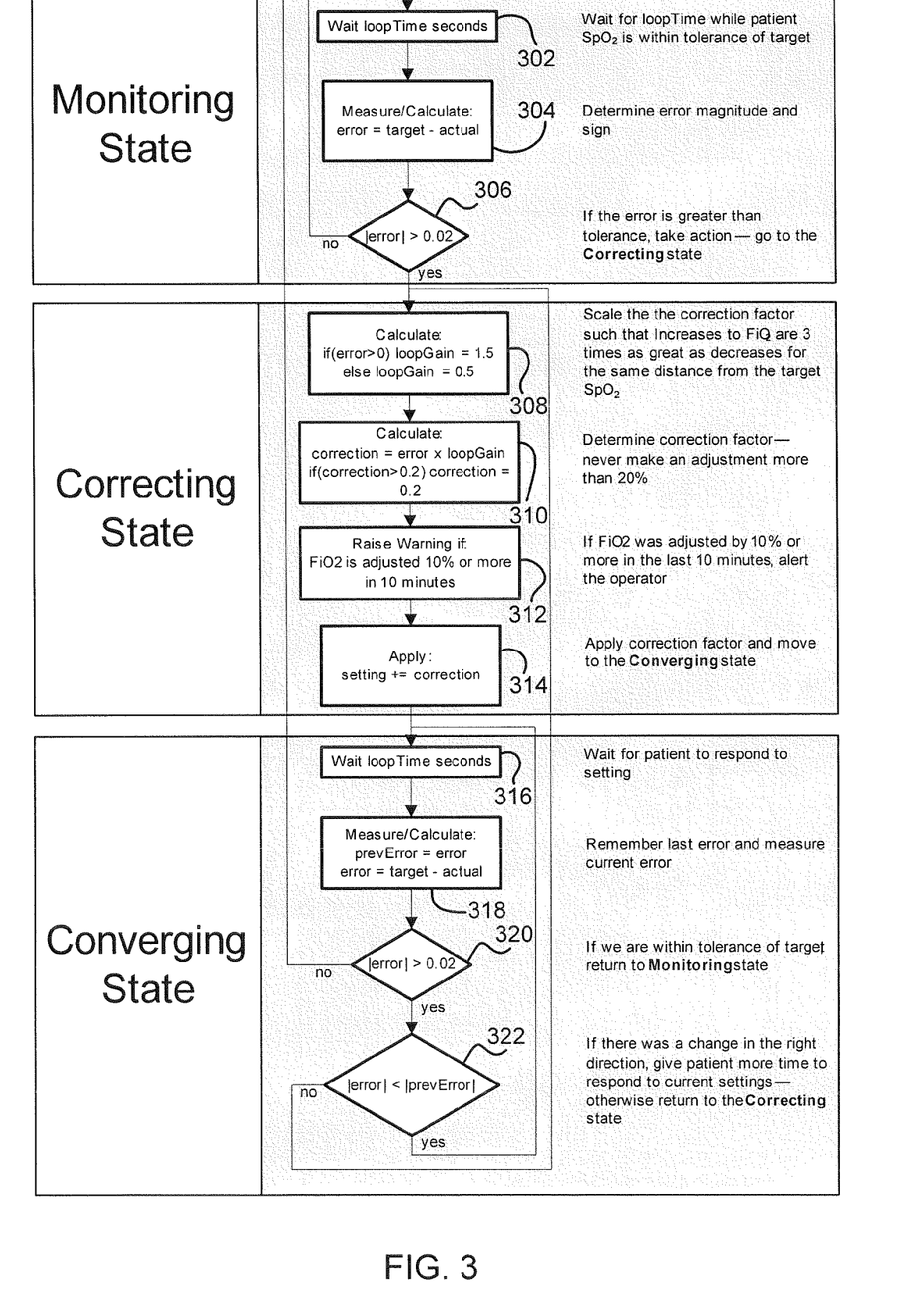
FIG. 3 is a flow diagram of an exemplary method for controlling $FlO_2$ supplied to a patient in accordance with an embodiment of the present disclosure.

Referring to FIG. 3, a flow diagram of an exemplary method for controlling $FlO_2$ supplied to a patient in accordance with an embodiment of the present disclosure is provided. The method includes three states: a monitoring state, a correcting state and a converging state. Initially, in step 302, the patient's target $SpO_2$ is monitored and a loop timer is started which determines a waiting period for when the patient's $SpO_2$ is within tolerance of the target. Next, in step 304, the error magnitude and sign of the monitored patient's $SpO_2$ is determined. In step 306, if the error is greater than tolerance, e.g., 0.02, corrective action is to be taken and the method moves to the correcting state. Otherwise, the method reverts back to step 302 and continues to monitor the patient.

In step 308, the correction factor is scaled such that increases to $FlO_2$ are 3 times as great as decreases for the same distance from the target $SpO_2$. Once the loop gain is determined in step 308, the correction factor is determined in step 310. It is to be noted that the adjustment is never to be more than 20%. In step 312, it is determined how much of an adjustment was made and, if the $FlO_2$ is adjusted by 10% or more in the last 10 minutes, an alert is issued to the operator. If the correction factor is within an acceptable limit, the correction factor is applied and the method moves to the converging state, in step 314.

In step 316, the loop timer is initiated again and the system will wait for the patient to respond. After the loop timer expires, the current error will be calculated, in step 318.

After the error is determined, in step 320, it is determined if the current error is within tolerance of the target. If the error is within the tolerance of the target, the method returns to the monitoring state and step 302. Otherwise, if the error is greater than the tolerance of the target, the method moves to step 322. In step 322, it is determined if the change was in the right direction by comparing the current error to the previous error. If the change was in the right direction, the method will revert to step 316 and will wait to allow the patient to respond to the current settings. However, if the change was in the wrong direction, the method will return to the correcting state at step 308 and the system will attempt to make further corrections.

Figure 4:
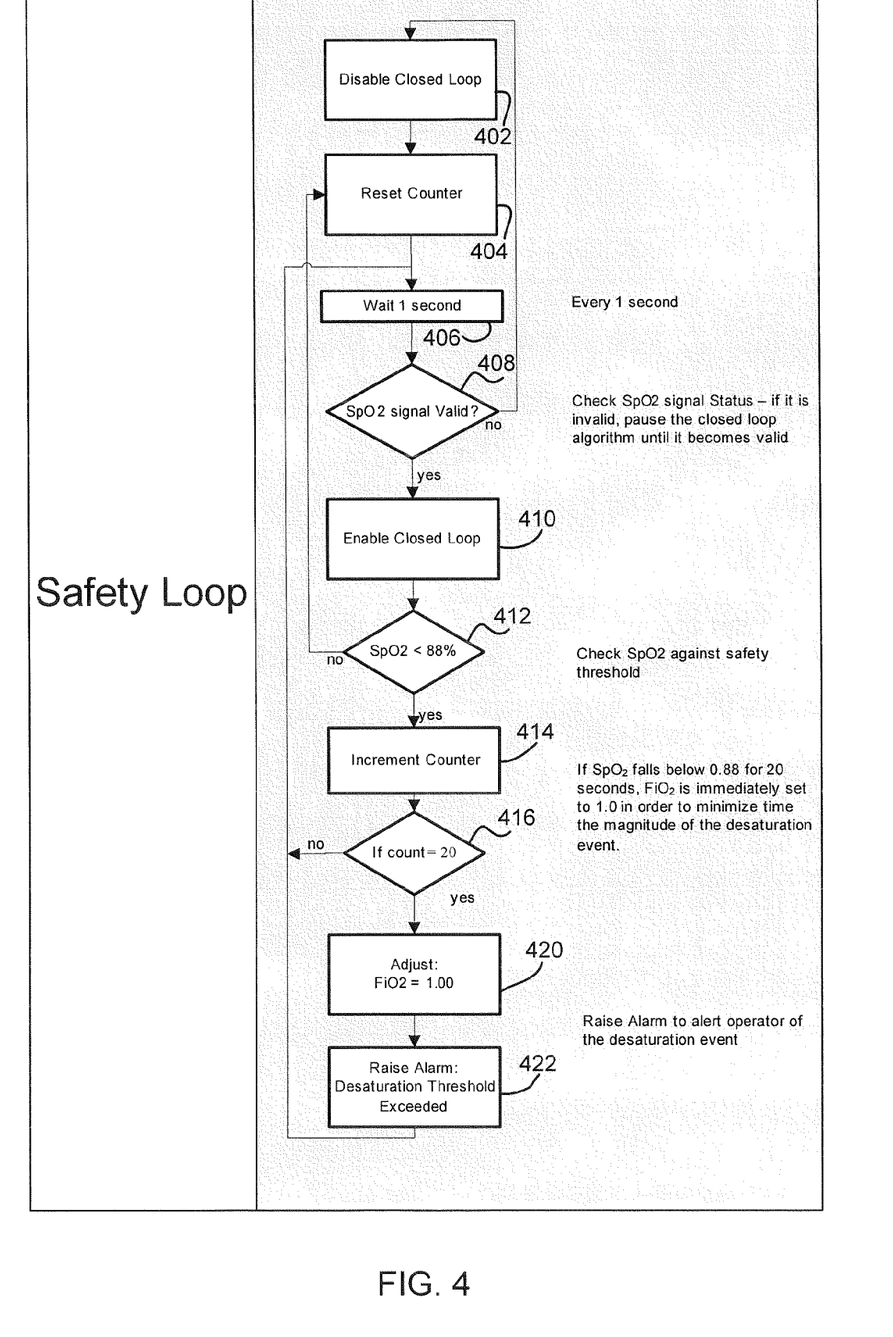
FIG. 4 is a flow diagram of an exemplary method of a safety loop employed in the ventilator in accordance with an embodiment of the present disclosure.

Referring to FIG. 4, a flow diagram of an exemplary method of a safety loop employed in the ventilator in accordance with an embodiment of the present disclosure is illustrated. Initially, in step 402, it is determined if the closed loop of FIG. 3 is disabled or not. If enabled, a counter is initially reset, in step 404, and the system will wait a predetermined time period, e.g., 1 second, for proper readings of the inputs, in step 406.

In step 408, the system will check the $SpO_2$ signal status using cyclic redundancy checking and additional error detection algorithms inherent in the $SpO_2$ sensor. If the $SpO_2$ signal is not valid, the closed loop control of the ventilator 102 will be disabled and an alert is issued. Otherwise, if the $SpO_2$ signal is valid, the closed loop control of the ventilator 102 is enabled. Once the closed loop is enabled, the controller 208 will check the $SpO_2$ signal against a safety threshold, e.g., is $SpO_2$ less than 88%. If the $SpO_2$ level is acceptable, the method returns to step 404 and continues to check for a valid signal. If the $SpO_2$ level is below 88%, a counter is started and incremented at step 414 and the $SpO_2$ level is checked again when the counter reached 20 seconds, at step 416. If the $SpO_2$ level falls below 0.88 for 20 seconds, the $FlO_2$ is immediately adjusted to 1.0 while an alert is issued, in step 420, to minimize the time and magnitude of the desaturation event. In step 422, an alarm is presented to the operator that the desaturation threshold has been exceeded and corrective action must be taken.

Although the disclosure herein has been described with reference to particular illustrative embodiments, it is to be understood that these embodiments are merely illustrative of the principles and applications of the present disclosure. Therefore numerous modifications may be made to the illustrative embodiments and other arrangements may be devised without departing from the spirit and scope of the present disclosure, which is defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '________' is hereby defined to mean . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed is:

1. A method for delivering oxygen to a patient with a mechanical ventilator, the method comprising:
   (a) supplying fractionally inspired oxygen ($FlO_2$) to a patient based on a target oxygen saturation ($SpO_2$), wherein the target $SpO_2$ is set a lower limit of clinical acceptability of $SpO_2$ for the patient to conserve oxygen;
   (b) monitoring $SpO_2$ returned from the patient;
   (c) determining an error between the monitored $SpO_2$ and the target $SpO_2$ and while the error is greater than a predetermined error iteratively performing,
   (d) determining a gain factor such that increases to $FlO_2$ are greater than decreases for a magnitude of the determined error;
   (e) determining a correction factor by multiplying the determined gain factor by the magnitude of the error;
   (f) applying the correction factor to the supplied $FlO_2$; and further comprising
   waiting a first predetermined time period before iteratively performing steps (c)-(f).

2. The method as in claim 1, wherein the first predetermined time period is about 40 seconds.

3. The method as in claim 1, wherein the gain factor is determined such that increases to $FlO_2$ are three times as great as decreases for the magnitude of the determined error.

4. The method as in claim 3, wherein if the correction factor is greater than a predetermined correction factor threshold, set the correction factor to the predetermined correction factor threshold.

5. The method as in claim 4, wherein the predetermined threshold is about 20 percent.

6. The method as in claim 4, further comprising, wherein if the supplied $FlO_2$ is adjusted more than a predetermined alert threshold with a second predetermined time period, issuing an alert to an operator of the mechanical ventilator.

7. The method as in claim 6, wherein the predetermined alert threshold is about 10 percent.

8. The method as in claim 6, wherein the predetermined alert threshold is about 10 percent and the second predetermined time period is about 10 minutes.

9. The method as in claim 3, further comprising:
determining if the monitored $SpO_2$ is below a predetermined safety threshold, wherein if the monitored $SpO_2$ is below the predetermined safety threshold for a predetermined safety time period, adjusting the $FlO_2$ to 1.0.

10. The method as in claim 9, wherein the predetermined safety threshold is about 88 percent.

11. The method as in claim 10, wherein the predetermined safety time period is about 20 seconds.

12. A system for delivering oxygen to a patient comprising:
a ventilator for supplying fractionally inspired oxygen ($FlO_2$) to a patient based on a target oxygen saturation ($SpO_2$), wherein the target $SpO_2$ is set at the lower limit of clinical acceptability of $SpO_2$ for the patient to conserve oxygen; and
an $O_2$ concentrator coupled to the ventilator for supplying oxygen to the ventilator,
wherein the ventilator monitors $SpO_2$ returned from the patient, determines an error between the monitored $SpO_2$ and the target $SpO_2$ and while the error is greater than a predetermined error, the ventilator iteratively determines a gain factor such that increases to $FlO_2$ are greater than decreases for a magnitude of the determined error, determines a correction factor by multiplying the determined gain factor by the magnitude of the error and applies the correction factor to the supplied $FlO_2$, and wherein the ventilator waits a first predetermined time period before iteratively applying the corrector factor to the supplied $FlO_2$.

13. The system as in claim 12, further comprising a patient ventilation circuit including a supply tube for supplying $FlO_2$ to the patient from the ventilator and a bidirectional connection for sending sensed or measured parameters of the patient to the ventilator.

14. The system as in claim 12, wherein the ventilator controls an output of the $O_2$ concentrator to maintain the corrected supplied $FlO_2$.

15. The system as in claim 12, wherein the ventilator mixes an output of the $O_2$ concentrator with ambient air to maintain the corrected supplied $FlO_2$.

16. The system as in claim 12, wherein the first predetermined time period is about 40 seconds.

17. The system as in claim 12, wherein the gain factor is determined such that increases to $FlO_2$ are three times as great as decreases for the magnitude of the determined error.

18. The system as in claim 17, wherein if the correction factor is greater than a predetermined correction factor threshold, the ventilator sets the correction factor to the predetermined correction factor threshold.

19. The system as in claim 18, wherein the predetermined threshold is about 20 percent.

20. The system as in claim 18, wherein if the supplied $FlO_2$ is adjusted more than a predetermined alert threshold with a second predetermined time period, the ventilator issues an alert to an operator of the ventilator.

21. The system as in claim 20, wherein the predetermined alert threshold is about 10 percent.

22. The system as in claim 20, wherein the predetermined alert threshold is about 10 percent and the second predetermined time period is about 10 minutes.

23. The system as in claim 17, wherein the ventilator determines if the monitored $SpO_2$ is below a predetermined safety threshold, and if the monitored $SpO_2$ is below the predetermined safety threshold for a predetermined safety time period, adjusts the $FlO_2$ to 1.0.

24. The system as in claim 23, wherein the predetermined safety threshold is about 88 percent.

25. The system as in claim 24, wherein the predetermined safety time period is about 20 seconds.

* * * * *